(12) United States Patent
Margaria et al.

(10) Patent No.: US 11,969,231 B2
(45) Date of Patent: *Apr. 30, 2024

(54) SYSTEM AND METHOD FOR 3D SCANNING

(71) Applicant: KONINKLIJKE PHILIPS N.V., Eindhoven (NL)

(72) Inventors: Elizabeth Powell Margaria, Pittsburgh, PA (US); Praveen Kumar Pandian Shanmuganathan, Monroeville, PA (US); Jonathan Sayer Grashow, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 303 days.

This patent is subject to a terminal disclaimer.

(21) Appl. No.: 17/159,566

(22) Filed: Jan. 27, 2021

(65) Prior Publication Data

US 2021/0148700 A1    May 20, 2021

Related U.S. Application Data

(62) Division of application No. 16/359,269, filed on Mar. 20, 2019, now Pat. No. 10,935,376.

(Continued)

(51) Int. Cl.
*A61B 5/00* (2006.01)
*G01B 11/25* (2006.01)
(Continued)

(52) U.S. Cl.
CPC .......... *A61B 5/0077* (2013.01); *A61B 5/0064* (2013.01); *G01B 11/25* (2013.01);
(Continued)

(58) Field of Classification Search
CPC .. G01B 11/2518; G06T 7/521; H04N 13/275; G06F 9/30003; G06V 20/64; G06V 40/16; G06V 10/145; A61B 5/0077
(Continued)

(56) References Cited

U.S. PATENT DOCUMENTS 10,373,344 B2    8/2019  Morifuji et al.
2007/0104472 A1  5/2007  Quan
(Continued)

FOREIGN PATENT DOCUMENTS

CN       1932847 A      3/2007
CN     105631891 A      6/2016
(Continued)

OTHER PUBLICATIONS

Chien, H-J et al., "Adaptive 3D Reconstruction system with improved recovery of miscoded region to automatically adjust projected light patterns", Image and Vision Computing New Zealand, 2008, 23rd International Conference, IEEE, NJ, pp. 106.

(Continued)

*Primary Examiner* — Sunghee Y Gray
(74) *Attorney, Agent, or Firm* — Michael W. Haas

(57) ABSTRACT

A system for capturing a 3D image of a subject includes a detection device which is structured to capture images of the subject and surrounding environment, a projection device which is structured to provide a source of structured light, and a processing unit in communication with the detection device and the projection device. The processing unit is programmed to: analyze an image of the subject captured by the detection device; modify one or more of: the output of the projection device or the intensity of a source of environmental lighting illuminating the subject based on the analysis of the image; and capture a 3D image of the subject with the detection device and the projection device using the (Continued)

modified one or more of the output of the projection device or the intensity of the source of environmental lighting illuminating the subject.

5 Claims, 6 Drawing Sheets

Related U.S. Application Data

(60) Provisional application No. 62/650,327, filed on Mar. 30, 2018.

(51) Int. Cl.
*G06F 9/30* (2018.01)
*G06T 7/521* (2017.01)
*G06V 10/145* (2022.01)
*G06V 20/64* (2022.01)
*G06V 40/16* (2022.01)
*H04N 13/275* (2018.01)

(52) U.S. Cl.
CPC ...... *G01B 11/2518* (2013.01); *G06F 9/30003* (2013.01); *G06T 7/521* (2017.01); *G06V 10/145* (2022.01); *G06V 20/64* (2022.01); *G06V 40/16* (2022.01); *H04N 13/275* (2018.05)

(58) Field of Classification Search
USPC .................................................. 356/600–612
See application file for complete search history.

(56) References Cited

U.S. PATENT DOCUMENTS

| | | |
|---|---|---|
| 2008/0204765 A1 | 8/2008 | Brinkmann et al. |
| 2008/0212106 A1 | 9/2008 | Brinkmann et al. |
| 2010/0091301 A1 | 4/2010 | Masuda |
| 2011/0063437 A1 | 3/2011 | Watanabe |
| 2012/0242800 A1* | 9/2012 | Ionescu ............... G06V 40/107 348/46 |
| 2015/0022644 A1 | 1/2015 | Appia |
| 2016/0150219 A1 | 5/2016 | Gordon et al. |
| 2016/0286202 A1 | 9/2016 | Romano et al. |
| 2017/0090111 A1 | 3/2017 | Teragawa |
| 2019/0293409 A1 | 9/2019 | Matsuda et al. |

FOREIGN PATENT DOCUMENTS

| | | |
|---|---|---|
| EP | 2889054 A1 | 7/2015 |
| JP | 2010091491 A | 4/2010 |
| JP | 2013126485 A | 6/2013 |
| JP | 2014182115 A | 9/2014 |
| KR | 20160139108 A | 12/2016 |
| KR | 20180023785 A | 3/2018 |
| WO | 2006109308 A1 | 10/2006 |
| WO | 2013175595 A1 | 11/2013 |
| WO | 2014149702 A1 | 9/2014 |
| WO | 2017090111 A1 | 6/2017 |
| WO | 2017127832 A1 | 7/2017 |

OTHER PUBLICATIONS

"Structured-light 3D Scanner", Wikipedia Downloaded for the Internet Mar. 14, 2019.
International Search Report for PCT/EP2019/057577 dated Mar. 26, 2019.

* cited by examiner

SYSTEM AND METHOD FOR 3D SCANNING

CROSS-REFERENCE TO RELATED APPLICATIONS

This application is a Divisional application of U.S. Ser. No. 16/359,269, filed Mar. 20, 2019, which claims the benefit of U.S. Provisional Application No. 62/650,327, filed on Mar. 30, 2018. These applications are hereby incorporated by reference herein.

BACKGROUND OF THE INVENTION

1. Field of the Invention

The present invention pertains to systems for carrying out 3D scanning of a subject. The present invention also pertains to methods for carrying out 3D scanning of a subject.

2. Description of the Related Art

Structured light scanning is a common method used in the 3D scanning industry to obtain 3-dimensional images of faces and objects. As shown schematically in FIG. 1, such method utilizes a light projector (different types of light can be used) which projects the light (typically in a pattern of parallel stripes) onto the face, body or object, and one or more cameras detect geometric distortions of the reflected pattern. FIG. 2 shows generally how the projected pattern is reconstructed into a 3D model.

Structured-light scanning is advantageous in terms of size: the technology allows for a structured-light scanning system to be contained within a small enclosure, such as a smart phone or other small form factors. However, conventional structured-light scanning methods and systems used therefore tend to produce inaccurate results when employed for facial scanning, such as would be employed in scanning a user's face in fitting a "custom" mask for use in an application such as CPAP.

SUMMARY OF THE INVENTION

Accordingly, it is an object of the present invention to provide a system and method that overcomes the shortcomings of conventional 3D image capturing systems and methods. As one aspect of the invention, a method of capturing a 3D image of a subject using a detection device and a projection device providing a source of structured light is provided. The method comprises: capturing an image of the subject with the detection device; analyzing the image; modifying one or more of: the output of the projection device or the intensity of a source of environmental lighting illuminating the subject based on the analysis of the image; and capturing a 3D image of the subject with the detection device and the projection device using the modified one or more of the output of the projection device or the intensity of the source of environmental lighting illuminating the subject.

Modifying the output of the projection device may comprise changing one or more of the wavelength or intensity of the output of the projection device.

Modifying the intensity of the source of environmental lighting illuminating the subject may comprise increasing the intensity of the source of environmental lighting.

Modifying the intensity of the source of environmental lighting illuminating the subject may comprise decreasing the intensity of the source of environmental lighting.

Modifying one or more of the output of a projection device or the intensity of a source of environmental lighting of the subject based on the analysis of the image may comprise modifying the output of the projection device by changing one or more of the wavelength and intensity of the output of the projection device.

The method may further comprise, after analyzing the image and before capturing the 3D image, providing instructions to the subject for an action to be taken by the subject to improve scan quality.

As another aspect of the invention, a system for capturing a 3D image of a subject is provided. The system comprises: a detection device which is structured to capture images of the subject and surrounding environment; a projection device which is structured to provide a source of structured light; and a processing unit in communication with the detection device and the projection device. The processing unit being programmed to: analyze an image of the subject captured by the detection device; modify one or more of: the output of the projection device or the intensity of a source of environmental lighting illuminating the subject based on the analysis of the image; and capture a 3D image of the subject with the detection device and the projection device using the modified one or more of the output of the projection device or the intensity of the source of environmental lighting illuminating the subject.

The processing unit may be programmed to modify the output of the projection device by changing one or more of the wavelength or intensity of the output of the projection device.

The processing unit may be programmed to modify the intensity of the source of environmental lighting illuminating the subject by increasing the intensity of the source of environmental lighting.

The processing unit may be programmed to modify the intensity of the source of environmental lighting illuminating the subject by decreasing the intensity of the source of environmental lighting.

The system may further comprise an output device and the processing unit may be further programmed to provide instructions to the subject via the output device for an action to be taken by the subject to improve scan quality after analyzing the image and before capturing the 3D image.

The detection device may comprise an RGB camera.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
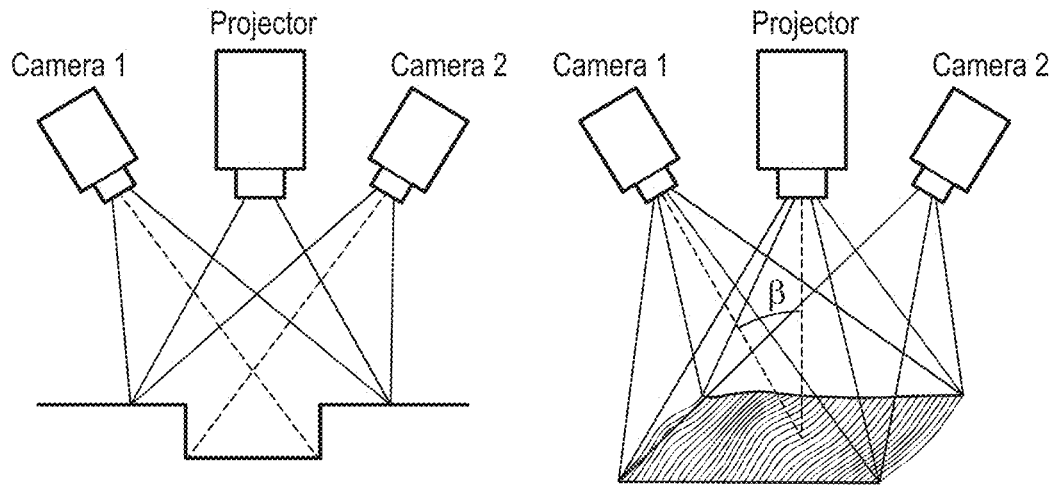
FIG. 1 is a schematic representation showing basic principles of structured-light 3D scanning.
Figure 2:
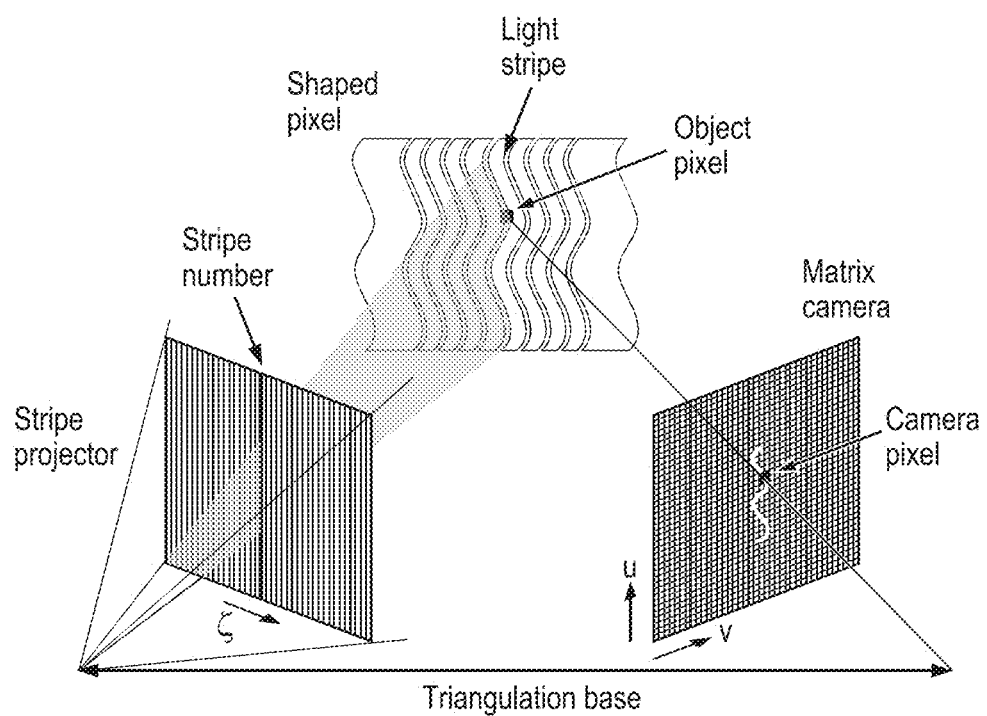
FIG. 2 is a schematic representation showing how a projected pattern is reconstructed into a 3D model.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Embodiments of the present invention are directed generally to systems and methods which increase the accuracy of structured-light scanning by automatically detecting the skin tone of a face, or the color of an object, using the RGB camera which already is present in most scanners, and changing the supporting (or ambient) light on the subject, and/or changing the wavelength/intensity of the projected structured light based on input from the RGB camera.

Figure 3:
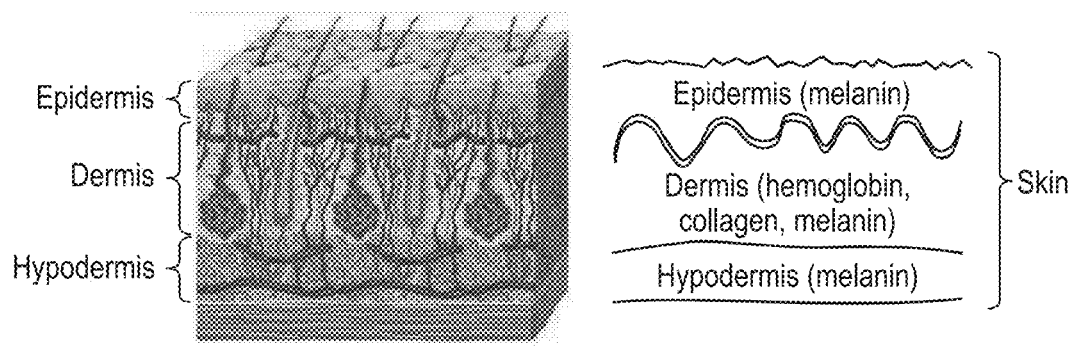
FIG. 3 is a schematic representation showing layers of human skin and chromophore content in each layer.
Figure 4:
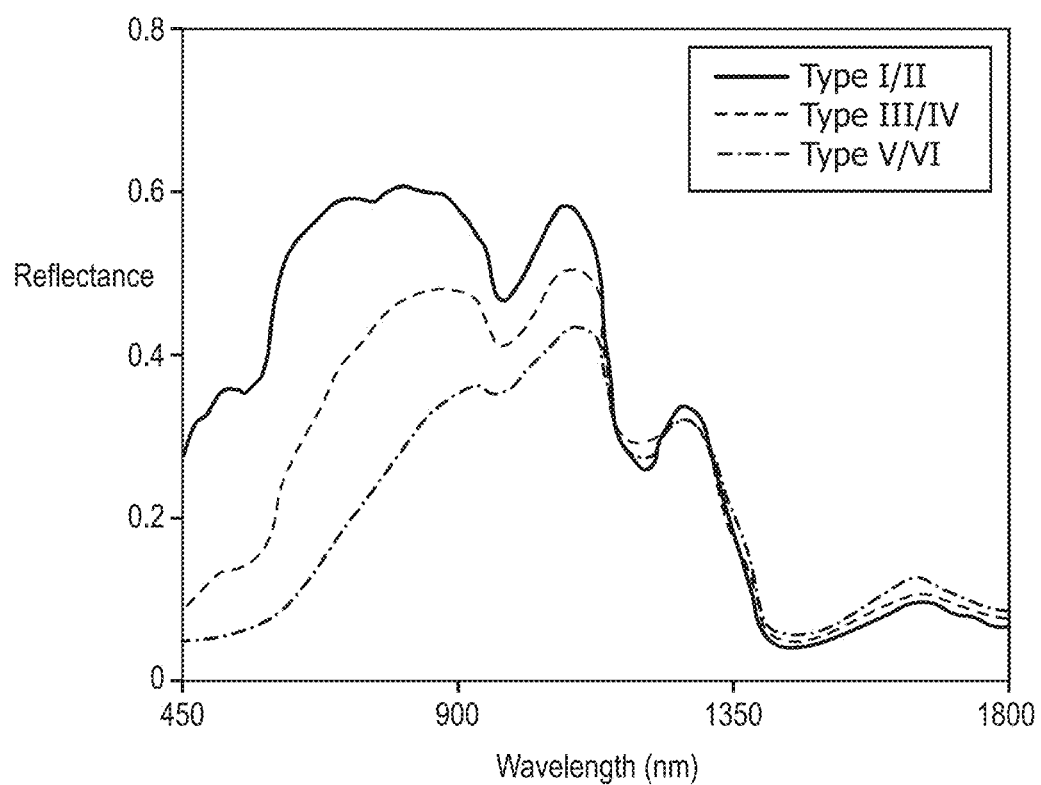
FIG. 4 is a graph showing a comparison of skin reflectance spectra for different skin complexions.

As discussed in the Background, structured-light scanning is advantageous in terms of size, the technology allows for a structured-light scanning system to be contained within a small enclosure, such as a smart phone or other small form factors. However, during facial scanning, the accuracy of the structured-light scanning method is compromised by the reflectance and absorption of human skin. In our experiments, it is evident that lighting conditions need to be changed depending on the skin complexion of the subject being scanned. This is because human skin is composed of different layers (i.e., epidermis, dermis, hypodermis), such as generally illustrated in FIG. 3, each layer containing differing amounts of components (chromophores) which have unique light scattering and absorbing properties. The main chromophores of human skin are melanin and hemoglobin. The amount of melanin present is higher in dark-skinned subjects and is lesser in light-skinned subjects. These differing amounts of chromophores in the skin, particularly melanin, cause light to reflect from different skin types at varying intensities. FIG. 4 shows skin reflectance for different skin types at wavelengths of light from 450-1800 nm. It can be seen from this plot that lighter skin (Type I/II) reflects more light from roughly 450 nm-1150 nm, whereas it reflects slightly less light around 1200 nm, and beyond 1350 nm.

Figure 5:
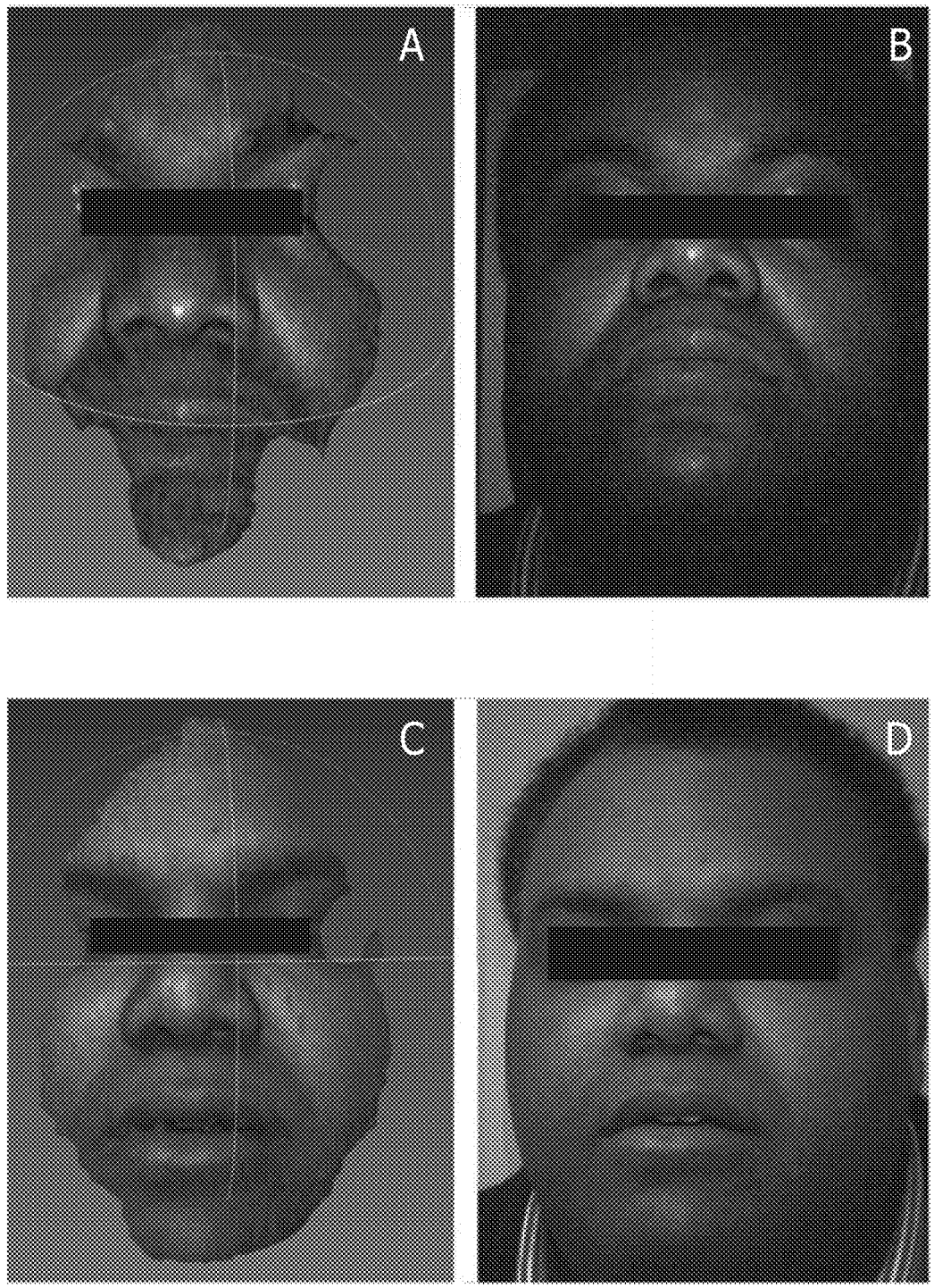
FIG. 5 shows photos of an individual having a high melanin content in their skin in a low light and higher light condition along with corresponding 3D scans obtained in such lighting conditions.

However, if the intensity of the structured light is increased, or if there is supporting light added, improved scans can be obtained. Scan A of FIG. 5 shows how too little ambient light can affect scan quality for an individual with higher melanin content in their skin, as shown in the corresponding photo B of FIG. 5. The darker skin of the individual has relatively less reflectance due to the large melanin content in the skin. Such decreased reflectance makes it difficult for the scanner to "see" the entire face, especially in low ambient light, thus generally resulting in the fragmented, incomplete scan. When more ambient light was added to illuminate the individual, such as shown in photo D of FIG. 5, the facial scan quality was improved significantly, such as shown in scan C of FIG. 5.

Figure 6:
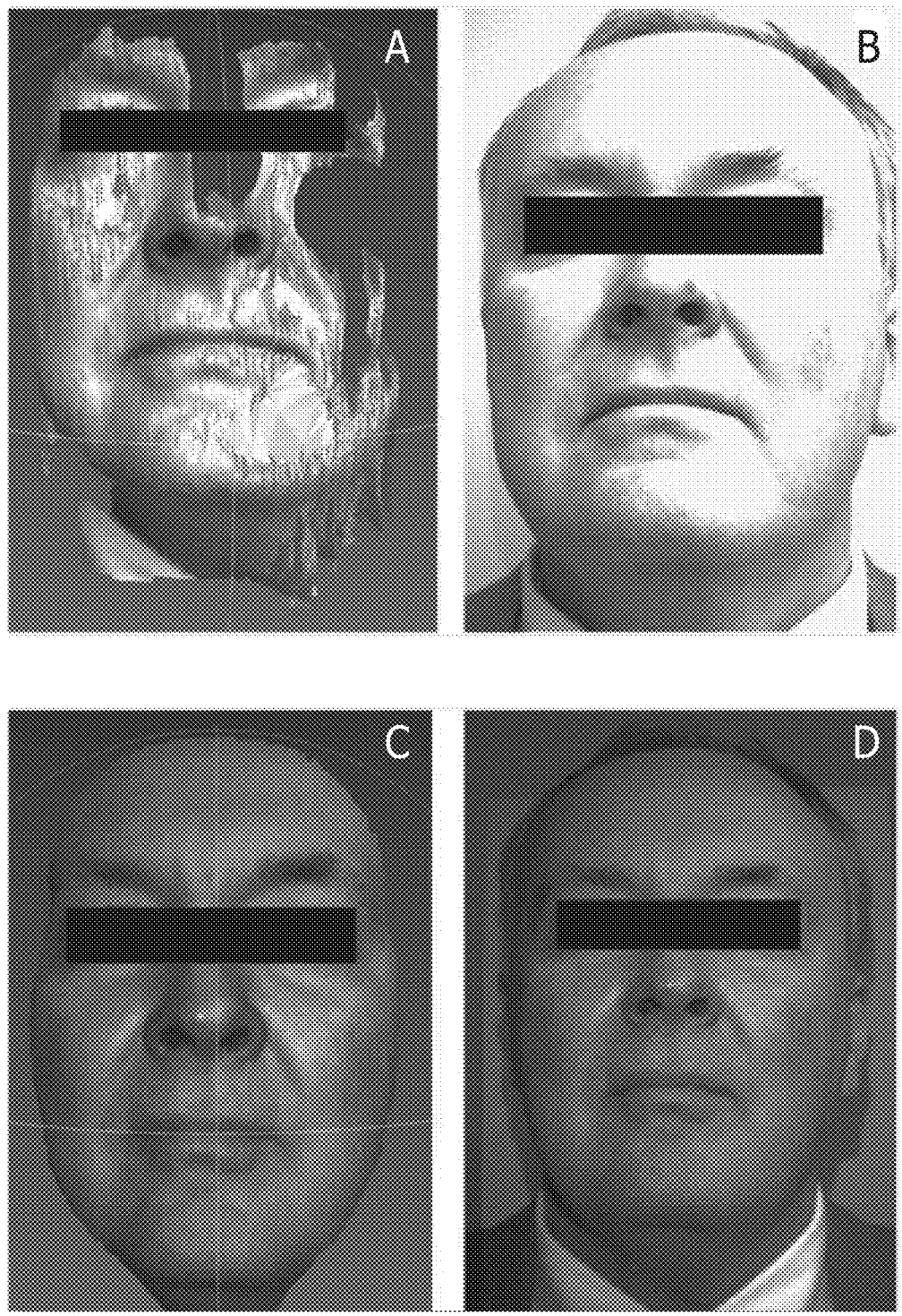
FIG. 6 shows photos of an individual having a low melanin content in their skin in a high light and lower light condition along with corresponding 3D scans obtained in such lighting conditions.

In contrast to the example of FIG. 5, individuals with lower melanin content appear to need less ambient light. FIG. 6 illustrates how changes in ambient light can affect scan quality for someone with lower melanin content in their skin. Too much ambient light, such as shown in photo B of FIG. 6, resulted in holes in the scan, and poor surface resolution, such as shown in scan A of FIG. 6. Less ambient light, such as shown in photo D of FIG. 6, resulted in much better scan quality, as shown in scan C of FIG. 6. Thus, it can be demonstrated that different skin tones can result in different scan qualities. In the preceding examples, changing the ambient light had a dramatic effect on scan quality. In these cases, a system that detected skin tone, and correspondingly changed the supporting light, could have improved the scan quality in an automated way.

Figure 7:
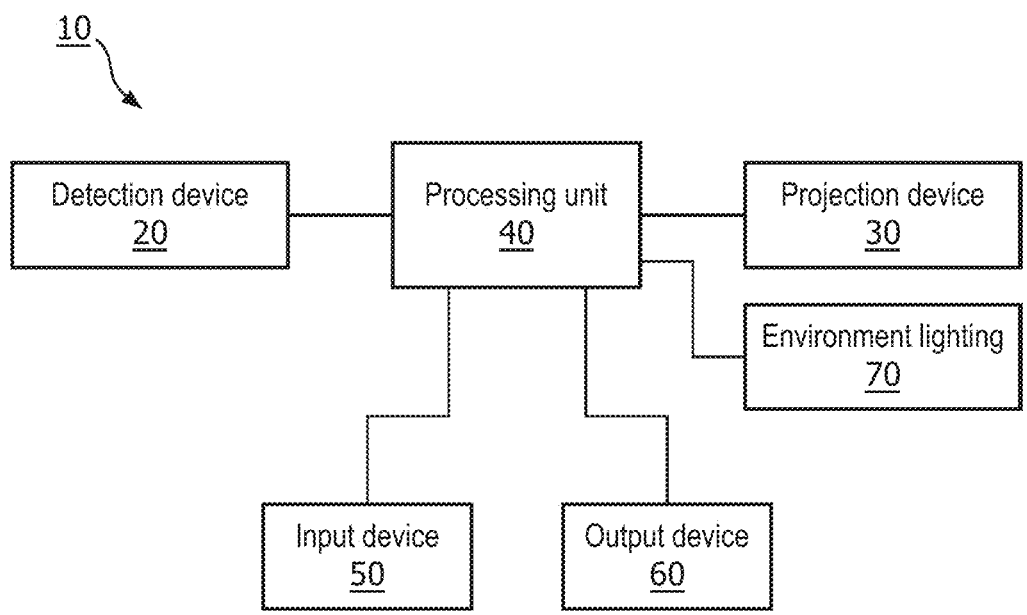
FIG. 7 is a schematic diagram of a system for obtaining a 3D scan of a subject in accordance with an example embodiment of the present invention.

FIG. 7 is a schematic diagram of a system 10 for obtaining 3D images of a subject in accordance with an example embodiment of the present invention. System 10 may be employed in carrying out 3D scanning methods in accordance with the present invention as described herein below. System 10 includes a detection device 20, which in an example embodiment of the present invention is in the form of an RGB camera which detects the skin tone or color of the subject being scanned (e.g., without limitation, a face, part of the body, object, etc.). Similar to conventional devices for carrying out structured-light scanning, system 10 further includes a projection device 30 which provides the source of the structured light used in the scanning process. As will be discussed further below, the wavelength and/or intensity of the light projected by projection device 30 can be selectively modified in order to optimize the scan for a particular subject in a particular environment.

Continuing to refer to FIG. 7, system 10 further includes a processing unit 40 which is in communication with detection device 20 and projection device 30 so as to control operation thereof and receive signals therefrom. Processing unit 40 includes a processor portion (not numbered) which may be, for example, a microprocessor, a microcontroller or some other suitable processing device, and a memory portion (not numbered) that may be internal to the processing portion or operatively coupled to the processing portion and that provides a storage medium for data and software executable by the processing portion for controlling the operation of system 10. The memory portion can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory.

Figure 8:
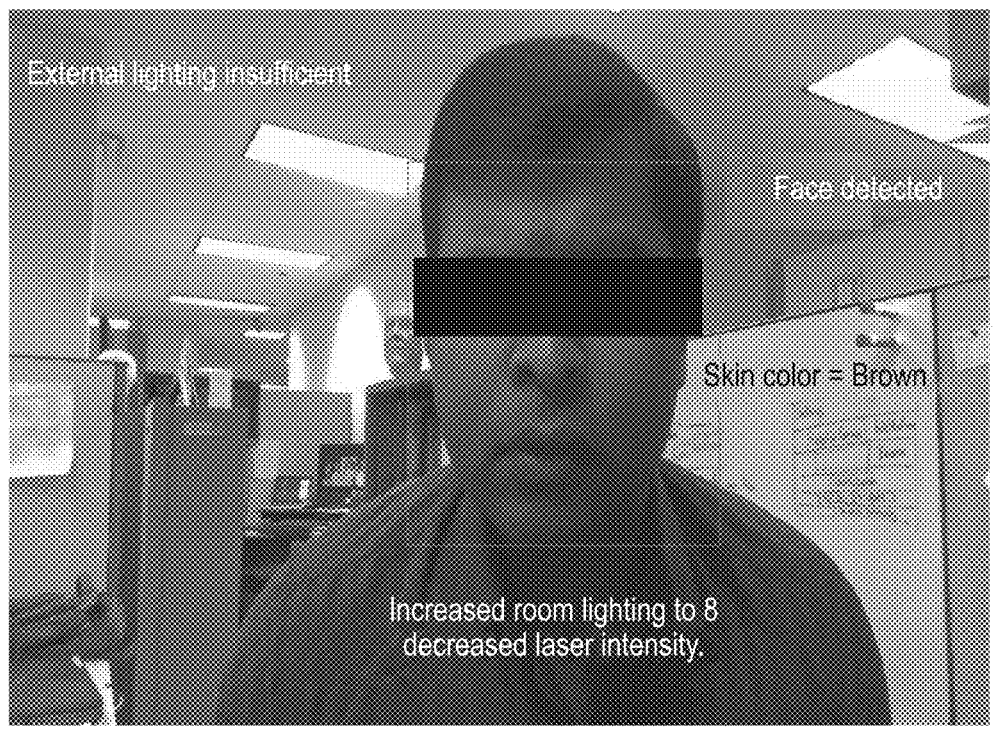
FIG. 8 shows an example analysis of an image carried out by an example embodiment of the present invention.
Figure 9:
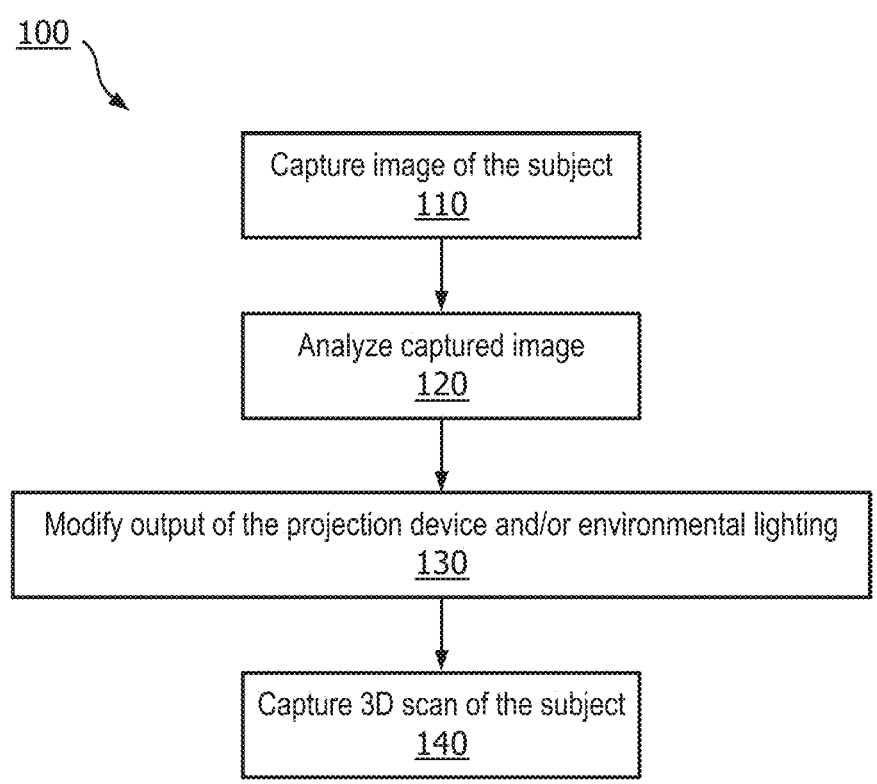
FIG. 9 is a schematic diagram of a method in accordance with an example embodiment of the present invention.

Processing unit 40 is programmed with a classifier which can be trained using known techniques to automatically detect faces in the frames captured by detection unit 20 using a given set of training images. Once the classifier is trained robustly enough to detect faces, a sliding window protocol is used to analyze pixels from the top left to the right bottom in the screen. As the striding layer reads the pixels in the screen, the pixel intensities are averaged to find the environment lighting and also the skin color of the individual within the face detector. This arrangement can be used as a feedback loop to adjust the lighting of the environment by reading the skin intensity of the subject and intensity of the laser projector. An example representation of this arrangement is illustrated in FIG. 8.

System 10 may also include: an input device 50 in communication with processing unit 40 for inputting of information to processing unit 40; an output device 60 for providing output from processing unit 40 to a user; or a combination input/output device for providing input to, or output from processing unit 40. System 10 may also include a number of sources of environmental lighting 70 which are controllable by processing unit 40. For example, environmental lighting 70 may include smart-lighting in the room in which the subject is being scanned which can be controlled automatically, i.e., increased/decreased, by processing unit 40. As another example, environmental lighting 70 may include a number of light sources housed in device 10 or distinct from device 10 which are separate from the lighting in the room but are controllable by processing unit 40.

Having thus described the basic components of an example 3D scanning device 10 in accordance with an example embedment of the present invention, an example method 100 for obtaining a 3D scan of a subject in accordance with an example embodiment of the present invention will now be described in conjunction with FIG. 8. Method 100 begins at 110 wherein an image of the subject is captured via detection device 20. Next, at 120, the image is analyzed by processing unit 40. During such analysis, the skin tone (e.g., light or dark) is determined of the subject being scanned. The environmental lighting illuminating the subject is also determined. Next, as shown at 130, one or both of the output of projection device 30 (e.g., wavelength, intensity) and/or environmental lighting 70 (e.g., intensity) is adjusted according to predetermined parameters in order to optimize scanning based on the skin tone and original lighting illuminating the subject. Optionally, instructions may be provided to the subject via output device 60 for improving scan quality. For example, such instructions may direct the subject to adjust their positioning (e.g., move closer, farther, turn, etc.) with respect to detection device 20. As another example, such instructions may direct the subject to cause a change in the environmental lighting (e.g., brighten, dim). Finally, an 3D scan of the subject is captured using detection device and projection device, as shown at 140.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A method of capturing a 3D image of a subject using a detection device, a projection device providing a source of structured light, an environment lighting illuminating the subject and a processing unit structured to control a source of the environment lighting, the method comprising:
   capturing an image of the subject with the detection device;
   analyzing the image;
   modifying an intensity of the source of the environment lighting by the processing unit based on the analysis of the image, wherein the source of the environment lighting illuminating the subject is separate from the source of structured light and
   capturing a 3D image of the subject with the detection device, the projection device and the environment lighting using the modified intensity of the source of environmental lighting illuminating the subject.

2. The method of claim 1, further comprising modifying an output of the projection device by changing one or more of a wavelength or intensity of the output of the projection device.

3. The method of claim 1, wherein modifying the intensity of the source of environment lighting illuminating the subject comprises increasing the intensity of the source of environment lighting.

4. The method of claim 1, wherein modifying the intensity of the source of environment lighting illuminating the subject comprises decreasing the intensity of the source of environment lighting.

5. The method of claim 1, further comprising, after analyzing the image and before capturing the 3D image, providing instructions to the subject for an action to be taken by the subject to improve scan quality.

\* \* \* \* \*